(12) United States Patent
Cerruti et al.

(10) Patent No.: US 8,167,937 B2
(45) Date of Patent: May 1, 2012

(54) ARTIFICIAL HEART

(75) Inventors: Aldo Cerruti, Lainate (IT); Romano Frederick Murri, Rome (IT); Marzia Murri, Rome (IT)

(73) Assignee: Genomnia S.r.l. (IT)

( * ) Notice: Subject to any disclaimer, the term of this patent is extended or adjusted under 35 U.S.C. 154(b) by 681 days.

(21) Appl. No.: 11/721,901

(22) PCT Filed: Dec. 20, 2005

(86) PCT No.: PCT/IB2005/003827
§ 371 (c)(1), (2), (4) Date: Oct. 7, 2009

(87) PCT Pub. No.: WO2006/067588
PCT Pub. Date: Jun. 29, 2006

(65) Prior Publication Data
US 2010/0016959 A1    Jan. 21, 2010

(30) Foreign Application Priority Data
Dec. 20, 2004    (IT) .............................. RM2004A0622

(51) Int. Cl.
*A61M 1/10*    (2006.01)

(52) U.S. Cl. ..................................................... 623/3.12
(58) Field of Classification Search ........... 623/3.1–3.27
See application file for complete search history.

(56) References Cited

FOREIGN PATENT DOCUMENTS

| | | |
|---|---|---|
| DE | 43 25 166 A1 | 2/1995 |
| DE | 196 16 125 A1 | 10/1997 |
| FR | 2 776 011 A | 9/1999 |
| IT | 1 152 339 B | 12/1986 |
| WO | WO97/43520 A | 11/1997 |

*Primary Examiner* — William H. Matthews
(74) *Attorney, Agent, or Firm* — Akerman Senterfitt

(57) ABSTRACT

A heart pump including a casing internally defining a substantially spherical cavity (10) housing: a rotating shutter (12) secured to the cavity (10) so as to be rotatable about a rotation axis; an oscillating shutter (14) secured to the rotating shutter (12) and rotatable relative to the latter about a rotation axis transverse to the rotation axis of the rotating shutter relative to the casing; a guide ring (18) secured to the oscillating shutter (14) such that the latter can rotate relative to the ring. The guide ring is arranged to move within a seal formed in the substantially spherical cavity (10) while lying in a substantially slanting plane relative to the rotation axis of the rotating shutter (12) and thereby making the rotating shutter rotate. This allows constructing an artificial heart of very small size that can be driven either by a motor member or by an induced muscle contraction.

16 Claims, 3 Drawing Sheets

ARTIFICIAL HEART

The present invention concerns an artificial heart, which can be operated for instance by means of a motor or by means of the contraction of a muscle The continuously increasing demand for a pump capable of replacing the action of the heart muscle, or even assisting it so as to reduce its fatigue condition and to allow partial operations on the heart or more effective therapies for recovering the whole or a better functionality, has lead to the research for a device, forming the subject matter of the present invention, which could be constructed so as to offer peculiar features, such as:

- size reduced to a minimum: actually, should the device be of support to the heart, a size allowing the least invasive thoracic implantation would be essential;
- maximum care in keeping blood flow free from haemolysis;
- a pumping flow such as to make fluid dynamics as close as possible, or even equal, to the original one;
- maximum reliability in time, attainable also through the reduction in the number of components and the attention to their sizes, as well as through further attentions that will become apparent from the description of the present patent.

It is an object of the present invention to provide a pump that can be realised so as to exhibit at least one of the above-listed features Such an object is achieved, according to the present invention, thanks to a device having the features according to claim 1.

In a preferred embodiment, the device according to the present invention, which can be used as an artificial heart pump, comprises a spherical pump of the Murri type, provided in turn with openings acting as ducts, said openings including at least one opening pair in the north region and one pair in the south region (relative to the rotation axis) and being controlled by the passage of the rotating vane In a preferred embodiment, the device according to the present invention comprises a disc intended to control the duct opening and/or closing depending on the rotating vane position In a preferred embodiment, the device according to the present invention comprises a guide ring that determining the mutual angle of the two vanes and also acting as a pulling member for the internal moving parts.

In a preferred embodiment, the device according to the present invention comprises an electric motor as a drive member for the guide ring In a preferred embodiment, the device according to the present invention comprises an electric motor as a drive member connected to the rotation axis of the rotating vane In a preferred embodiment, the device according to the present invention is operable by a muscle mass suitably connected to the guide ring and forming the drive member for the ring.

In a preferred embodiment, the device according to the present invention comprises a guide ring having a gear shaped external surface, which can be connected with the outside of the structure In a preferred embodiment, the device according to the present invention is equipped with vanes, a portion of which, or at least of some of which, includes a resilient surface capable of absorbing or conditioning the pressor peaks and the volume that can be pumped at each rotation.

In a preferred embodiment, the device according to the present invention comprises pockets arranged between the vane surfaces and capable of protecting and conditioning the movement of the blood flow.

In a preferred embodiment, the device according to the present invention comprises fluid-tight members at the vane points that are the closest to the spherical surface In a preferred embodiment, the device according to the present invention comprises fluid-tight members at the vane intersection points In a preferred embodiment, the device according to the present invention comprises fluid-tight members in the sliding region of the guide ring The opportunity to have a pulsating flow, and not a continuous one, to reduce as much as possible the number of components, to avoid or reduce all parts capable of causing haemolysis, to have a size as small as possible, to control the internal pressure values, and especially the depression values, to have an electrically powered mechanical drive with minimum bulk and consumption, to be mechanically operable by means of biological energy (through a muscle contraction), to avoid one-way or other valves, to have a final cost that can be accepted and sustained by the public health system, to have a management and drive cost as small as possible, to require no kind of structure maintenance for very long periods, are peculiarities representing the object of the research work performed and of the particular embodiments that will be disclosed hereinafter Those peculiarities make the above-mentioned device exploitable for conducting an artificial heart of new design Further advantages attainable by the present invention will become more apparent from the following detailed description, given by way of non-limiting example with reference to the accompanying schematic Figures.

The following description of the various components is to be intended as a set of sequential steps of a construction The manufacturer could decide to perform all steps or even to perform one or more of them at a time, in case exploitation of all devices is not deemed suitable at that moment because such devices are not considered to be essential for constructing a functional and highly reliable heart pump.

Thus, the present patent shows, for explanatory purposes and without limiting intentions, the possibility of such actions and embodiments that allow the device of the present patent to be used as an artificial heart.

Figure 7:
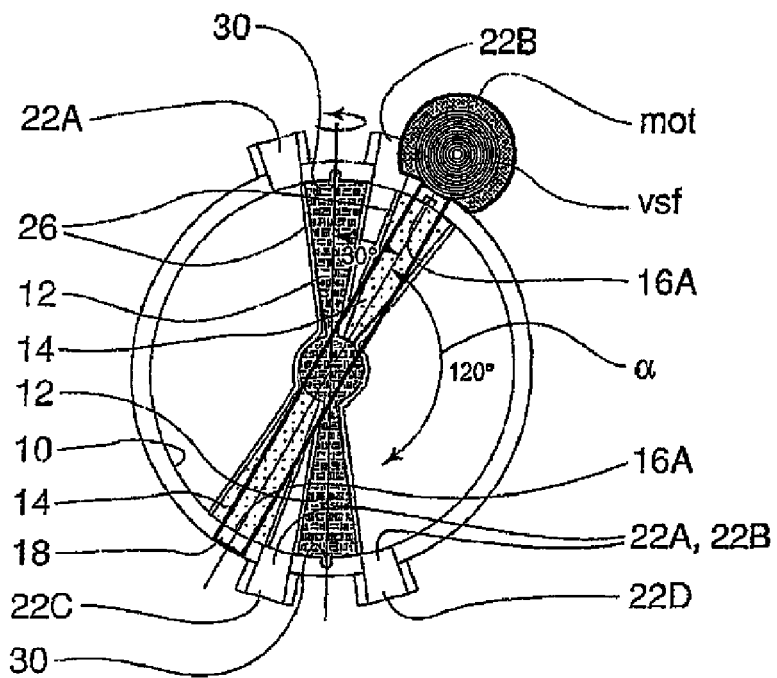
FIG. 7 is a cross sectional side view of a fourth embodiment of a device according to the present invention.

A pump according to the invention, which is also capable of replacing the natural heart pump or having a supporting and ancillary action therefor, can be derived from the spherical pump disclosed in Italian Patent Application No. 27266 A/82, filed on 6 Aug. 1982 by Romano Murri and entitled "Meccanismo spaziale destinato ad assolvere una pluralità di funzioni o combinazioni di funzioni" (Spatial mechanism intended to perform a plurality of functions or function combinations) The basic structure of that pump can be taken up, while integrating thereinto a group of devices capable of allowing the aforesaid mechanism to be developed into an artificial heart In its basic construction, the device includes an external housing or casing, inside which a spherical cavity 10 is defined, housing in turn a rotating shutter 12 The latter has for instance the shape of a circular disc with the same diameter as the sphere (less the necessary tolerances allowing the disc motion). Said rotating shutter 12 is connected to said hollow spherical surface 10, in correspondence with a diameter thereof, by means of two projections, pins (FIG. 7) or other suitable securing means 30, in such a way that the shutter is rotatable about such a diameter and divides the space within the spherical surface into two portions with the same volume A second shutter 14, having for instance the same shape and size as rotating shutter 12, is hinged to shutter 12 along the diameter perpendicular to the rotation axis of rotating shutter 12 The second shutter in turn divides the space within the spherical surface into four portions having in pairs variable volumes, depending on the relative angle between shutters 12 and 14.

In the present description, rotating shutter 12 and oscillating shutter 14 are also referred to as first disc 12 and second disc 14, or also as rotating vane 12 and oscillating vane 14.

Two projections 16A, 16B, or other suitable engaging means, are located at the two points perpendicular to the hinge in the circumference of the second disc and are arranged to condition the mutual angular movement of both discs, as will be disclosed in greater detail below A guide ring 18 is inserted into the thickness of the spherical surface. The ring is rotatable within an own seat—for instance shaped as an annular groove, not shown—which is offset (inclined) by a few degrees relative to the rotation axis of rotating shutter 12. Projections 16A, 16B of second disc 14 in turn engage two cavities 20A, 20B formed internally of guide ring 18 and diametrically opposed to each other Upon a complete rotation of rotating shutter 32 about its rotation axis, second disc 14 will perform a relative angular movement such as to make cyclically vary the volume of the four chambers into which the spherical cavity housing both discs 12, 14 is divided, until resuming its original position For instance, in the embodiment shown in FIG. 7, guide ring 18 is off-axis by 30° relative to the rotation axis of rotating shutter 12, and the angular movement of oscillating shutter 14, which will be of 120°, is denoted by α

As a consequence, at each rotation, the pumping capacity of the system is up to at most twice the volume of spherical cavity 10 itself. Actually, if oscillating disc 14 moves by 180°, each spherical portion will pump a volume equal to 50% of the volume of sphere 10: since four chambers are provided, this would result in a pumping capacity of twice the internal volume. Since a sphere is the solid exhibiting the maximum volume with a minimum surface, and since the described device is capable, at each rotation, of pumping up to twice its internal volume, a pump as small as possible is obtained, which therefore is the most suitable for a thoracic implantation with the minimum possible invasive impact The need of being able to generate a pulsating flow, as similar as possible, or even equal, to the natural heart flow, adds to the great importance of the minimum size When implementing the device so that the movement drive is induced by an electric motor, it is possible to operate as follows. Guide ring 18 is the member determining the pumping capacity, and the angle of the ring plane relative to the axis of totaling disc 12 makes the pumping capacity pass from 0 at an angle of 90°, to 2V at an angle of 0°, where V denotes the internal volume of the sphere When using guide ring 18 not only as the member generating the oscillating movement of oscillating rotor 14—or oscillating disc 14—but also as the motion-inducing member, by externally shaping the same ring 18' as a gear or a rack (FIG. 5), it is possible (always by way of explanation and without any limiting character, as in the previous illustrations), to act so that an oscillating movement of oscillating shutter 14 corresponds to a constant rotation movement of ring 18': this consequently results in the generation of a pulsating flow, which will be stationary at the point where pins or projections 16A, 16B pass at the minimum distance from the rotation axis of rotating shutter 12, and will have the maximum flow rate at the point where pins or projections 16A, 16B are offset by 90° relative to the rotation axis of rotating shutter 12

Figure 1:
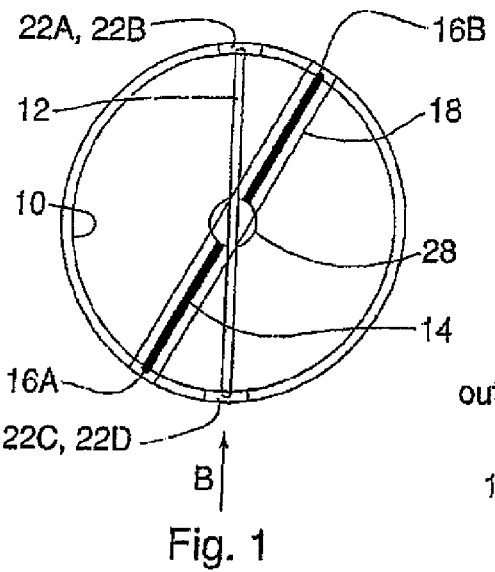
FIG. 1 is a cross sectional side view of a first embodiment of a device according to the present invention.
Figure 2:
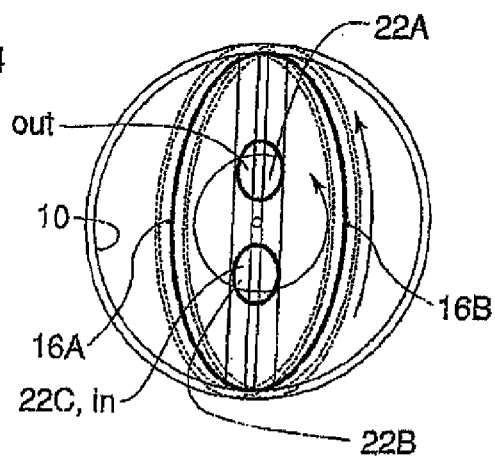
FIG. 2 is a cross-sectional top view of the device of FIG. 1.
Figure 5:
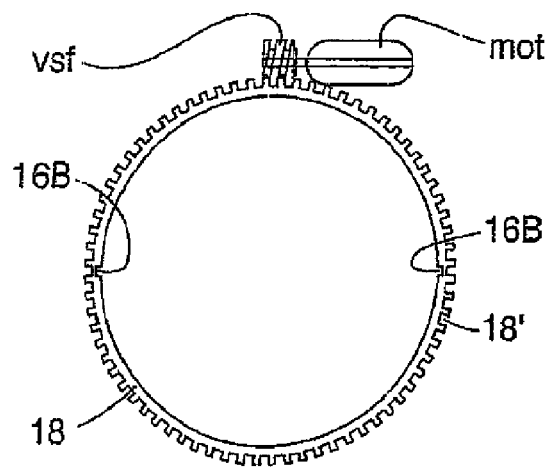
FIG. 5 shows the guide ring, the driver and the pinion-gear wheel link by means of which the driver can actuate the guide ring, in a third embodiment of a device according to the present invention.
Figure 6:
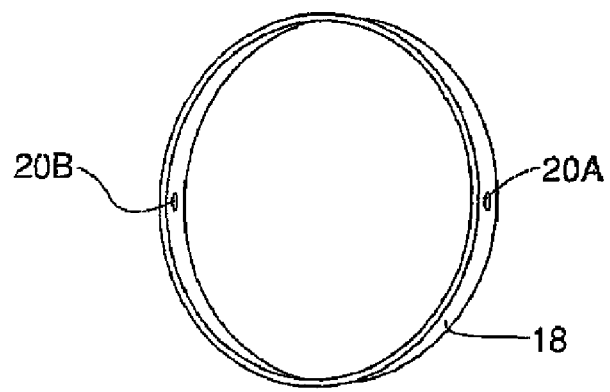
FIG. 6 shows a guide ring without links to the outside.

In FIG. 5, reference symbol VSF denotes the pinion of the gear wheel—worm system driving guide ring 18', whereas reference symbol MOI denotes the electric motor driving pinion VSF In the basic embodiment, in order both to reduce the number of components and consequently to obtain the maximum reliability and duration in time, two pairs of openings 22A, 22B, 22C, 22D are provided in the spherical surface near the rotation axis of rotating disc 12, two openings—22A, 22B—being provided in the north portion and two—22C, 22D—in the south portion. Such openings form the end portions of the ducts through which the blood flow enters the venous circulatory system on the one side and the arterial circulatory system on the other side. Ducts 22A, 22B, 22C, 22D for admission and emission of the blood flow are also denoted IN and OUT in FIG. 2, where 16A is the pin on the viewer side and the rotation direction is as indicated by the arrows The above construction is a function of the research for attaining a pulsating flow as well as a reduction of the haemolysis possibility. Being the latter generated or at least made easier by pressor and depressor peaks, in this embodiment, at each rotation by 180° a flow is obtained having a behaviour that keeps the pressure as low as possible and that increases the flow rate when the flow velocity increases, and decreases the flow rate when the flow velocity decreases Consequently, at the passage of the external vane surfaces, the flow is substantially stationary, thereby reducing to a minimum the risk of haemolysis by abrasion, should blood be introduced with force into ducts that are closed and opened.

Figure 3:
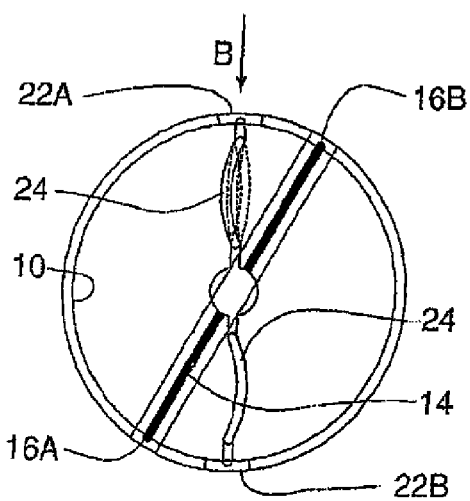
FIG. 3 is a cross sectional side view of a second embodiment of a device according to the present invention.
Figure 4:
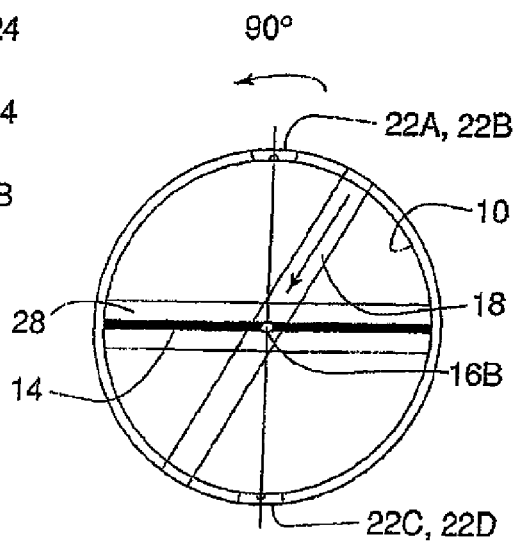
FIG. 4 is a cross sectional side view of the device of FIG. 1, and more particularly it shows the positions of the rotating and oscillating shutters upon a 90° rotation of the rotating shutter.

Moreover, should it be desired or necessary to further decrease the positive and negative pressure values within the system, this can be attained by providing resilient portions 24 in the surfaces of discs 12 and/or 14, (FIG. 3), or other resilient systems capable of absorbing the pressor peaks and/or limiting the flow rate of the fluid.

Figure 8:
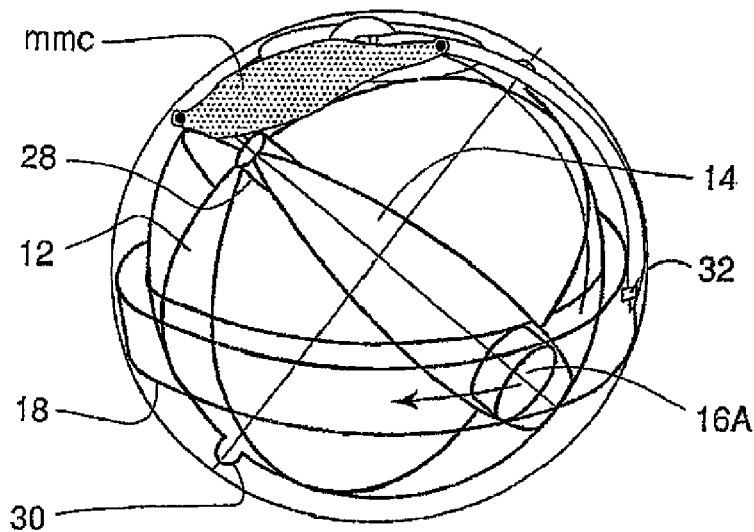
FIG. 8 is a cross sectional side view of a fifth embodiment of a device according to the present invention.
Figure 9:
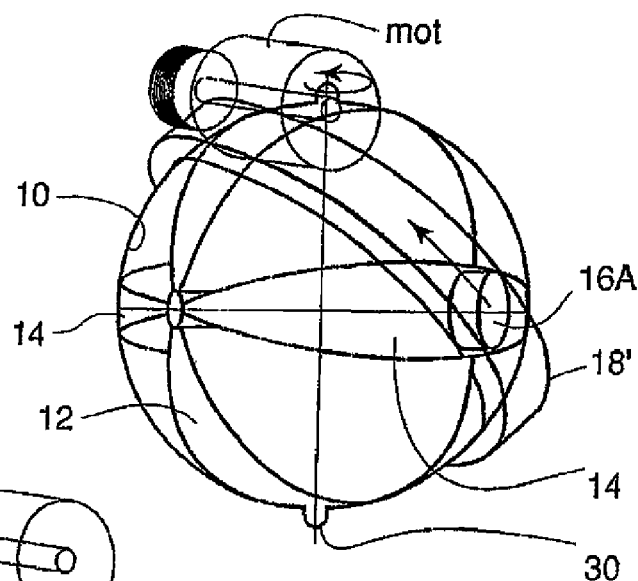
FIG. 9 is a perspective view of a sixth embodiment, in which a heart pump according to the present invention is operated by a motor connected to the guide ring.
Figure 10:
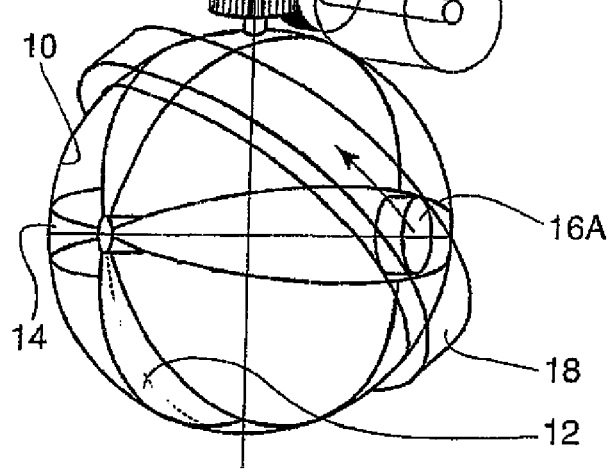
FIG. 10 is a perspective view of a seventh embodiment, in which a heart pump according to the present invention is operated by a motor which in turn directly drives the first disc, also referred to as rotating disc, and makes it rotate about its rotation axis.

Still in order to be careful of haemolysis, if necessary, internal pockets could be provided inside pumping portions 26 (FIG. 7), which pockets do not bring blood in contact with the "hinge" member 28 (FIGS. 1, 4, 8, 9) connecting discs 12, 14 at their centres and conditioning their mutual movement FIG. 9 shows a possible association between an electric motor and a pump system driven through a worm connected to the motor and a suitable rack provided on the external surface of guide ring 18

FIG. 8 shows the drive of guide ring 18 obtained by means of a contractile muscle mass (denoted MMC), which, under the action of a natural or electrically induced stimulus, causes by its contraction the movement of guide ring 18 and consequently the operation of the heart pump Reference numeral 32 denotes a drive member for guide ring 18 Clearly, such an embodiment would rid the system of the need for an electrical powering of the motor and hence would free the patient of one of the recurrent slaveries created by the use of a pumping system driven by an electric motor Several changes and modifications can be made to the embodiments described hereinbefore, without departing from the scope of the present invention.

LIST OF SOME REFERENCE SYMBOLS 12 rotating vane
18 guide ring
16A, 16B pins connecting the oscillating shutter and the guide ring
14 oscillating shutter
22A, 22B, 22C, 22D blood ducts
28 hinge connecting the rotating vane and the oscillating shutter

The invention claimed is:

1. An artificial heart, including a pump comprising:
a casing internally defining a substantially spherical cavity;
a rotating shutter, housed within the substantially spherical cavity and secured thereto so as to be rotatable about an own rotation axis;
an oscillating shutter, also housed within the substantially spherical cavity and secured to the rotating shutter so as to be rotatable relative to the latter about a rotation axis transversal to the rotation axis of the rotating shutter relative to the casing;
a guide ring, secured to the oscillating shutter so as to allow the latter to rotate relative to the same guide ring, wherein the guide ring is arranged to move within a seat formed in the substantially spherical cavity while lying in a plane substantially slanting relative to the rotation axis of the rotating shutter and making thereby the rotating shutter rotate,
wherein at least one of the rotating shutter and the oscillating shutter is provided with resilient walls, diaphragms or other means capable of absorbing the pressure peaks and/or limiting the flow rate of fluid being pumped.

2. The artificial heart as claimed in claim 1, wherein the oscillating shutter is hingedly connected to the rotating shutter so as to be rotatable about an axis substantially perpendicular to the rotation axis of the rotating shutter relative to the casing.

3. The artificial heart as claimed in claim 1, wherein the oscillating shutter is hingedly connected to the guide ring so as to be rotatable relative to the ring about an axis substantially perpendicular to the hinge and/or rotation axis of the oscillating shutter relative to the rotating shutter.

4. The artificial heart as claimed in claim 1, wherein the casing includes one or more suction openings and one or more delivery openings, preferably located close to the regions where the rotating shutter is hinged to the same casing.

5. The artificial heart as claimed in claim 1, wherein the rotation axis of the rotating shutter relative to the casing and the projection thereof on the plane where the guide ring lies define between them an angle substantially ranging from 5° to 90°.

6. The artificial heart as claimed in claim 1, comprising a driver arranged to operate the rotating shutter through the guide ring.

7. The artificial heart as claimed in claim 1, comprising a driver arranged to operate the oscillating shutter through the rotating shutter.

8. The artificial heart as claimed in claim 6, wherein the driver comprises a rotating motor.

9. The artificial heart as claimed in claim 6, wherein the driver comprises a rotating motor and the guide ring is provided with a toothing that can be engaged by the driver.

10. The artificial heart as claimed in claim 1, arranged to be connected to a driver so that the latter operates either the rotating shutter through the guide ring or the oscillating shutter through the rotating shutter, wherein the driver is configured to include a muscle or muscle fibers.

11. The artificial heart as claimed in claim 10, wherein said driver is configured to include a muscle or muscle fibers, and is connected to a drive member for operating the guide ring.

12. The artificial heart as claimed in claim 8, wherein the rotating motor is an electric motor.

13. An artificial heart, including a pump comprising:
a casing internally defining a substantially spherical cavity;
a rotating shutter, housed within the substantially spherical cavity and secured thereto so as to be rotatable about an own rotation axis;
an oscillating shutter, also housed within the substantially spherical cavity and secured to the rotating shutter so as to be rotatable relative to the latter about a rotation axis transversal to the rotation axis of the rotating shutter relative to the casing;
a guide ring, secured to the oscillating shutter so as to allow the latter to rotate relative to the same guide ring, wherein the guide ring is arranged to move within a seat formed in the substantially spherical cavity while lying in a plane substantially slanting relative to the rotation axis of the rotating shutter and making thereby the rotating shutter rotate,
said artificial heart being arranged to be connected to a driver so that the latter operates either the rotating shutter through the guide ring or the oscillating shutter through the rotating shutter, wherein the driver is configured to include a muscle or muscle fibers.

14. The artificial heart as claimed in claim 13, wherein said driver is configured to include a muscle or muscle fibers, and is connected to a drive member for operating the guide ring.

15. The artificial heart as claimed in claim 5, wherein the rotation axis of the rotating shutter relative to the casing and the projection thereof on the plane where the guide ring lies define between them an angle substantially ranging from 15° to 70°.

16. The artificial heart as claimed in claim 15, wherein the rotation axis of the rotating shutter relative to the casing and the projection thereof on the plane where the guide ring lies define between them an angle substantially ranging from 30° to 50°.

* * * * *